US 6,648,863 B2

(12) United States Patent
Reever

(10) Patent No.: US 6,648,863 B2
(45) Date of Patent: Nov. 18, 2003

(54) APPARATUS AND METHODS FOR TREATING THE URINARY BLADDER

(75) Inventor: Kenneth Reever, Hopedale, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/957,206

(22) Filed: Sep. 20, 2001

(65) Prior Publication Data

US 2002/0045868 A1 Apr. 18, 2002

Related U.S. Application Data

(60) Provisional application No. 60/233,881, filed on Sep. 20, 2000.

(51) Int. Cl.[7] .............................. A61M 1/00; A61F 2/04
(52) U.S. Cl. ...................... 604/327; 604/258; 604/544; 623/12
(58) Field of Search ..................... 128/885; 604/544, 604/325, 327, 329, 335, 258, 910; 623/23.64, 23.65, 12

(56) References Cited

U.S. PATENT DOCUMENTS

| | | | | |
|---|---|---|---|---|
| 3,953,897 A | * | 5/1976 | Chevallet et al. | ........ 623/23.65 |
| 4,044,401 A | * | 8/1977 | Guiset | ..................... 623/23.65 |
| 5,019,096 A | * | 5/1991 | Fox et al. | ..................... 600/36 |
| 5,445,626 A | | 8/1995 | Gigante | |
| 5,479,945 A | | 1/1996 | Simon | |
| 6,458,867 B1 | * | 10/2002 | Wang et al. | ................. 523/105 |

OTHER PUBLICATIONS

Manhatten et al., "ICN Patient Handbook—Living with Interstitial Cystitis in 2001" www.ic.network.com, Aug. 17, 2001, 8 pages.

* cited by examiner

*Primary Examiner*—Weilun Lo
*Assistant Examiner*—Michael Bogart
(74) *Attorney, Agent, or Firm*—Testa, Hurwitz, & Thibeault, LLP

(57) ABSTRACT

Disclosed are devices and methods for treating disease in a urinary bladder. The devices include a bladder liner for insertion into the urinary bladder and catheters positioned within the urinary bladder to carry urine from the ureters to an outside collection container. The bladder liner and catheters are constructed of biocompatible materials and are configured to create a seal with the urethra and ureters. The bladder liner may be adapted to deliver medicinal agents to the urinary bladder. Methods of treating disease in the urinary bladder include isolating urine from the bladder wall to allow sufficient time for the bladder wall to heal e.g., by implanting the aforementioned devices. Healing or pain relief may be enhanced by instilling pharmaceutical agents between the liner and bladder wall without dilutional effects.

18 Claims, 10 Drawing Sheets

APPARATUS AND METHODS FOR TREATING THE URINARY BLADDER

CROSS-REFERENCE TO RELATED APPLICATION

This application incorporates by reference, and claims priority to and the benefit of, U.S. Provisional Patent Application Ser. No. 60/233,881, which was filed on Sep. 20, 2000.

TECHNICAL FIELD

The invention generally relates to treating a urinary bladder.

BACKGROUND

Interstitial cystitis (IC) is a chronic inflammation or irritation of the urinary bladder wall that is estimated to affect between 500,000 and 1,000,000 people in the U.S. (approximately 90% female). The primary symptoms of IC are urinary urgency, frequency, and often-severe pelvic and perineal pain. The similarity of the symptoms of IC with other bladder diseases, such as urinary tract infections (UTI), urethritis, urethral syndrome, trigonitis, prostatitis, dysuria, and nocturia has caused difficulty in the diagnosis of the disease. After other similar bladder diseases are ruled out and a cystoscopic examination of the bladder wall reveals characteristic signs of IC, including small petechial hemorrhages or larger Hunner's Ulcers, IC is usually diagnosed.

The biological cause of IC remains undetermined. The theory that IC is caused by a bacterial infection is controversial. IC patients routinely test negative for infection in standard urinalysis. On the other hand, several studies have shown antibiotic treatment regimens to alleviate symptoms for IC patients. Another possible cause is a defect in the epithelial permeability barrier of the bladder surface glycosaminoglycans (GAG). Once the bladder wall loses the protective coating of GAG, irritative components and potentially pathogenic bacteria in the urine can lead to the inflammation or irritation associated with IC. Another line of research indicates that activated mast cells, which are associated with pain and irritation, are involved in the pathology of IC. Studies have shown that IC patients have an increased level of activated mast cells in the tissues of the bladder wall.

Currently there is no permanent cure for IC in the majority of patients. Treatment of IC with drug therapy has been proven to be the most effective means of alleviating symptoms. Oral medications for IC include bladder-coating agents, antidepressants, antihistamines, antispasmodics, and anesthetics. The effectiveness of oral medications is limited by the circulating concentration of the drug in the blood stream. To address this limitation, many IC patients elect to undergo a procedure called urinary bladder instillation, in which a therapeutic solution is pumped into the bladder through a urethral catheter. The solution, which may be composed of one or a combination of medications, is held in the bladder for a "dwell time" before the bladder is drained or voided. This procedure allows the treatment of the urinary bladder wall directly with high concentrations of medicine. Despite the drawbacks of a limited dwell time for the medication to take effect and the necessary mixture of medication with urine, bladder instillation may be the most effective treatment currently available for IC.

SUMMARY OF THE INVENTION

The current urinary bladder instillation procedure for IC patients can be made more effective by increasing the dwell time and/or by using medication undiluted by urine. The invention generally relates to devices and ways for increasing dwell time in bladder instillations and/or for preventing dilution of the medication(s) used in bladder instillations.

Generally, the invention can feature a device for substantially isolating urine from the urinary bladder wall to give the bladder mucosal layer sufficient time to heal. The device can include a bladder, liner, or sack designed to fit inside the urinary bladder. The liner functions as an inner bladder for the urinary bladder and serves to protect the urinary bladder wall from contacting urine. Preventing urine from contacting the urinary bladder wall serves multiple therapeutic purposes. First, it allows the urinary bladder wall to be treated with medications without the medications being diluted by urine. Second, because the medications applied to the urinary bladder wall are prevented from mixing with the urine, they are not flushed out of the body following the voiding of the bladder. Third, the urinary bladder wall is protected from the caustic nature of the urine allowing for a more rapid healing process.

In general, the invention also can feature a system of catheters that connect to the ureteral orifices proximal to the urinary bladder and convey urine to an exterior urine collection bag or container. This device would provide similar therapeutic benefits as the urinary bladder liner by preventing urine from collecting in the urinary bladder or contacting the urinary bladder wall in any significant quantity. This device generally uses an external urine collection container to collect any urine flow resulting from the urinary bladder by-pass.

In one aspect, the invention relates to a medical device including a urinary bladder liner. The liner is adapted to fit within a patient's urinary bladder. The liner has a reservoir and two inlet orifices that are adapted to sealably connect to respective ends of the patient's ureters and an outlet orifice adapted to extend into the patient's urethra. The liner isolates urine from the urinary bladder. In various embodiments of the invention, the outlet orifice is adapted to sealably connect to the urethra and/or extend through the urinary sphincter and/or connect to a catheter that extends through the urinary sphincter. In other embodiments of the invention, the inlet orifices are connected to catheters that are adapted to sealably connect to the respective ureter openings. Alternatively, the catheters are adapted to extend through the patient's ureters and into the patient's kidneys. The distal ends of the inlet catheters may be coiled to fit in a kidney basin. The inlet catheters may include a plurality of fins mounted on exterior surfaces of the catheters and adapted to form a liquid-impermeable seal with a wall of each ureter.

In further embodiments, the outlet orifice or outlet catheter is made of a material sufficiently flexible so that the orifice or catheter can be completely compressed by the urinary sphincter. In addition, the sealable connections can be made with a biocompatible adhesive. Alternatively, the sealable connections can be created by the expansion of an outer wall diameter of an end of the catheter that contacts the body, which functions to fix the catheter end in place and to form a liquid-impermeable seal. In addition, the liner can be made of a pliant material, and/or a material chosen from silicone, vinyl, polyethylene, PVC, latex, ethylene vinyl acetate, and polypropylene, and/or a material that stretches and shrinks. Also, the liner can be coated with a heparin-like drug or a slippery material, such as a hydrogel, on the outer surface.

In yet another aspect, the invention relates to an apparatus for isolating urine from a patient's urinary bladder. The apparatus includes a first catheter and a second catheter, each including a proximal and a distal end. The proximal ends of the first and second catheters are adapted to sealably connect to the patient's ureter walls. The distal ends of the first and second catheters pass through the patient's urinary sphincter. Alternatively, the first and second catheters may each pass through a suprapubic incision in the patient's abdominal wall. The apparatus also includes an external urine collection container that is connected to the distal ends of the first and second catheters. In one embodiment, the first and second catheters include valves disposed between the distal ends of the catheters and either a distal end of the patient's urethra or the suprapubic incisions. The valves control the flow of urine to the collection container.

In one embodiment, the first and second catheters are joined together to form a third catheter. A proximal end of the third catheter is connected to and joins the distal ends of the first and second catheters. The distal end of the third catheter passes through the patient's urinary sphincter. Alternatively, the third catheter may pass through a suprapubic incision in the patient's abdominal wall. An external urine collection container is connected to a distal end of the third catheter. In some embodiments, the third catheter includes a valve disposed between either a distal end of a urethra or the suprapubic incision and the distal end of the third catheter for controlling the flow of urine to the collection container. In some embodiments, the seals are composed of biocompatible adhesives and/or the catheters are composed of materials comprising biocompatible plastics. In addition, the catheters can be made of materials chosen from silicone, vinyl, polyethylene, PVC, latex, ethylene vinyl acetate, and polypropylene.

In still another aspect, the invention relates to a method of treating urinary bladder diseases. The method includes the steps of isolating urine from a urinary bladder and treating the urinary bladder with appropriate medications. Appropriate medications include oral medications and/or topical medications. Typically, topical medications are instilled between a wall of the bladder and the bladder liner. The step of isolating the urine from the urinary bladder includes inserting a urinary bladder liner into the bladder. In another method, the step of isolating urine from the urinary bladder includes inserting an apparatus that carries urine from the ureter orifices to an external urine collection container. In one embodiment, the apparatus exits the patient's body through the urinary sphincter. In another embodiment, the apparatus exits the patient's body through one or more suprapubic incisions through the patient's abdominal wall.

These and other objects, along with advantages and features of the present invention herein disclosed, will become apparent through reference to the following description of embodiments of the invention, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings.

DESCRIPTION

Figure 1:
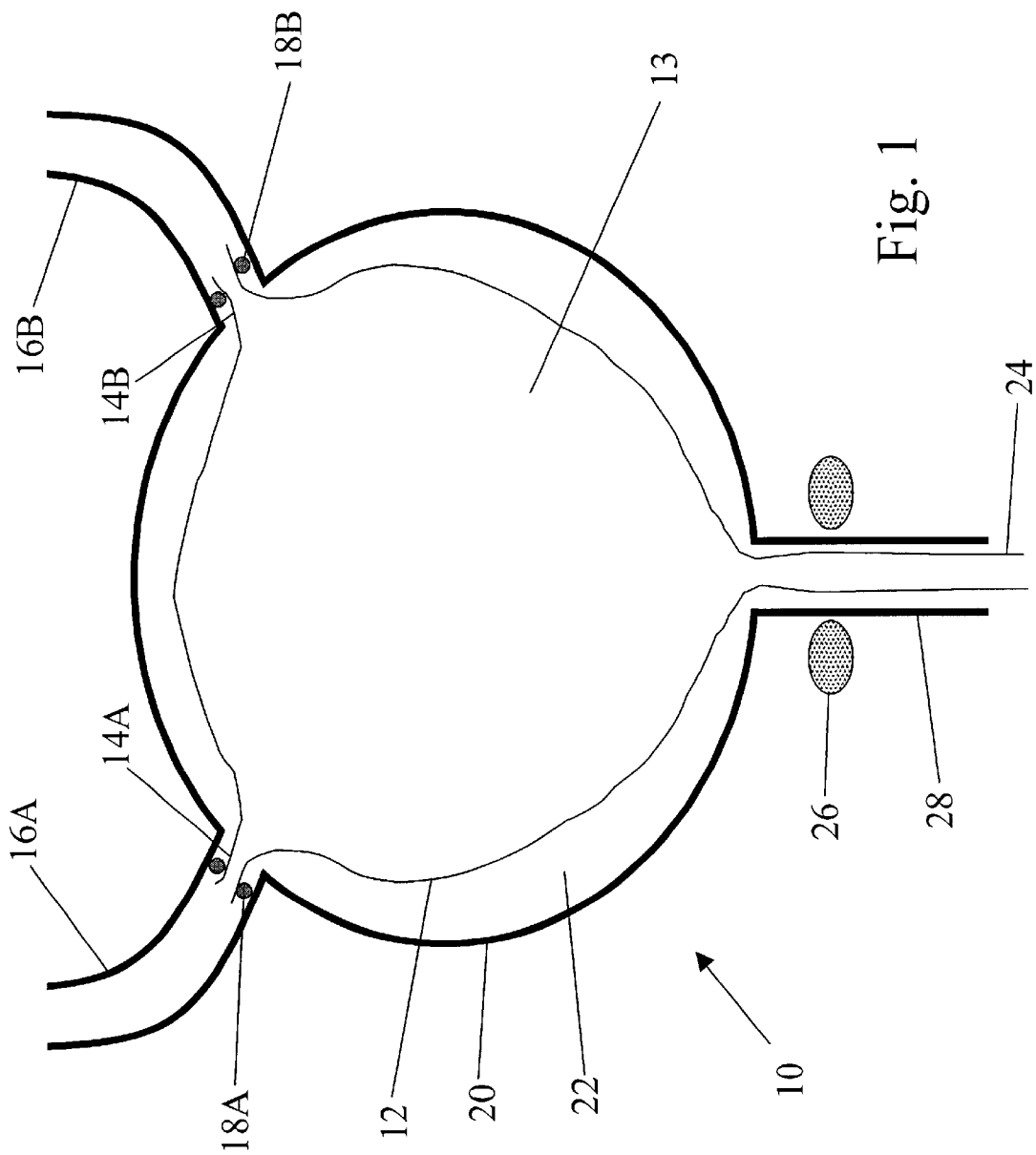
FIG. 1 is a depiction of a bladder liner that is designed to fit inside a patient's urinary bladder. The bladder liner possesses three orifices, two of which are positioned to interface with the patient's two ureters. The material of the bladder liner at the two inlet orifices extends into the orifice of the ureter and is fixed in place by a sealant. The outlet orifice of the bladder liner is the outlet tube that extends into the patient's urethra. This device provides for urinary continence by maintaining sphincter function.

FIG. 1 depicts a device 10 for isolating and preventing contact of urine with the urinary bladder wall 20. Urine normally flows from the kidneys into the ureters 16A,B, which drain into the urinary bladder 22. Urine is held in the urinary bladder 22 until the urinary sphincter 26 relaxes, allowing urine to flow from the bladder 22 through the urethra 28 and out of the body. The device 10 prevents urine from collecting directly in the urinary bladder 22, thus preventing contact of urine with the urinary bladder wall 20. Isolation of urine from the urinary bladder wall 20 has therapeutic benefits in the treatment of bladder diseases, infections, and disorders. Specifically, isolating urine from the urinary bladder wall 20 allows medications within the bladder 22 to function more effectively. Isolating urine from the urinary bladder 22 also allows the urinary bladder wall 20 to be treated with medications without the medications being diluted by urine, which lessens the strength of the medication, or being flushed out of the body following the voiding of the bladder 22, which greatly lessens the effective treatment time. Urine has a known caustic effect on cells. In a healthy urinary bladder 22, specialized epithelial cells line the surface of the urinary bladder wall 20 and are well adapted to survive the caustic environment that urine creates. Isolating urine from the urinary bladder 22 allows epithelial cells that are damaged or are in a diseased state to better recover from disease or fight infection while in a non-caustic environment.

In the embodiment of the invention shown in FIG. 1, a liner 12 is designed to fit inside the urinary bladder 22. The liner 12 is constructed from an impermeable but highly flexible and elastic material. The liner 12 forms a reservoir 13 for collecting urine therein. Such materials include vinyl, polyethylene, PVC, latex, silicone, ethylene vinyl acetate, and polypropylene. The liner 12 is constructed with two inlet orifices 14A,B that are adapted to sealably connect to the opening of the respective ureters 16A,B. The seals 18A,B between the ureters 16A,B and inlet orifices 14A,B prevent urine from leaking into the urinary bladder 22 and insure the flow of urine into the reservoir 13 of the liner 12. The outlet orifice 24 of the bladder liner 12 is adapted to extend into the urethra 28, which directs the flow of urine through the urethra 28 and out of the body. The outlet orifice 24 is shown extending past the urinary sphincter 26; however, the outlet orifice 24 does not have to extend past the urinary sphincter 26 so long as the outlet orifice 24 is situated to prevent backflow of urine into the bladder 22. This device allows the sphincter 26 to maintain normal function.

Figure 2:
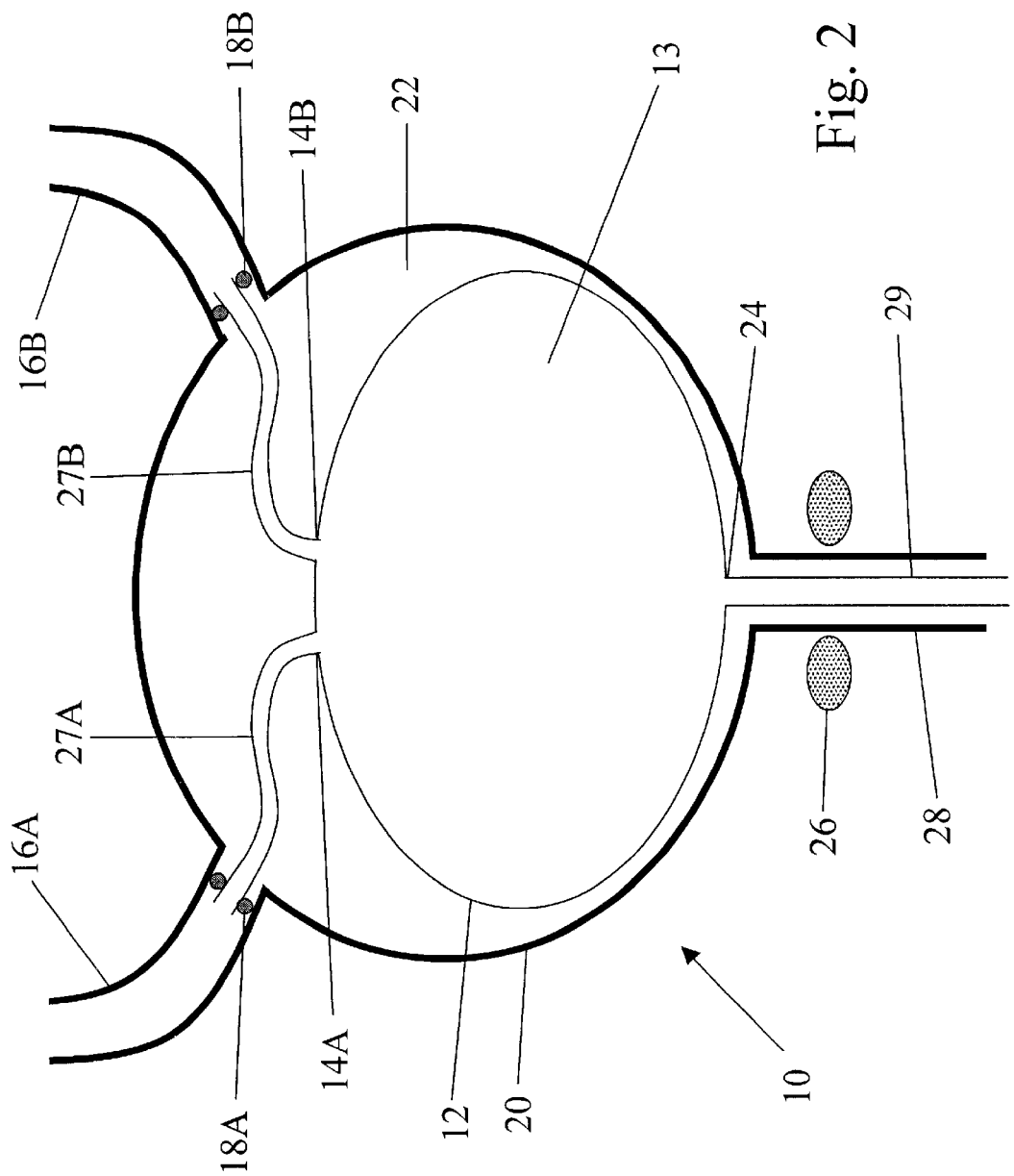
FIG. 2 is a depiction of a bladder liner that is designed to fit inside a patient's urinary bladder. Three catheters lead from the bladder liner. The two catheters that are situated on one side of the bladder liner are sealed to the patient's two ureters. The third catheter, which is generally situated on the opposite side of the bladder liner, extends into the patient's urethra past the urinary sphincter. This device provides for patient continence by maintaining sphincter function.

Another embodiment of the invention is shown in FIG. 2. A liner 12 is designed to fit inside the urinary bladder 22. The liner 12 is constructed from an impermeable material. The liner 12 includes a reservoir 13 formed therein and is constructed with two inlet orifices 14A,B that are connected directly to two inlet catheters 27A,B. The inlet orifices 14A,B and catheters 27A,B may be joined by use of a fitting or any suitable bonding process. The open ends of the two catheters 27A,B are adapted to sealably connect to the openings of the respective ureters 16A,B. Sealing may be accomplished through mechanical means, such as the use of bioadhesive(s), o-ring(s), or soft radial fins. The seals 18A,B are disposed between the ureters 16A,B and input catheters 27A,B to prevent urine from leaking into the urinary bladder 22 and insure the flow of urine into the liner 12. An outlet catheter 29 is connected to the outlet orifice 24 of the bladder liner 12 and is adapted to extend through the urethra 28. The outlet catheter 29 directs the flow of urine through the urethra 28 and out of the body. The outlet catheter 29 extends into the urethra 28 past the point in the urethra that is constricted by the urinary sphincter 26. The outlet catheter 29 is composed of a material sufficiently flexible so that the catheter 29 can be completely compressed by the urinary sphincter 26, thus preventing incontinence.

Figure 3:
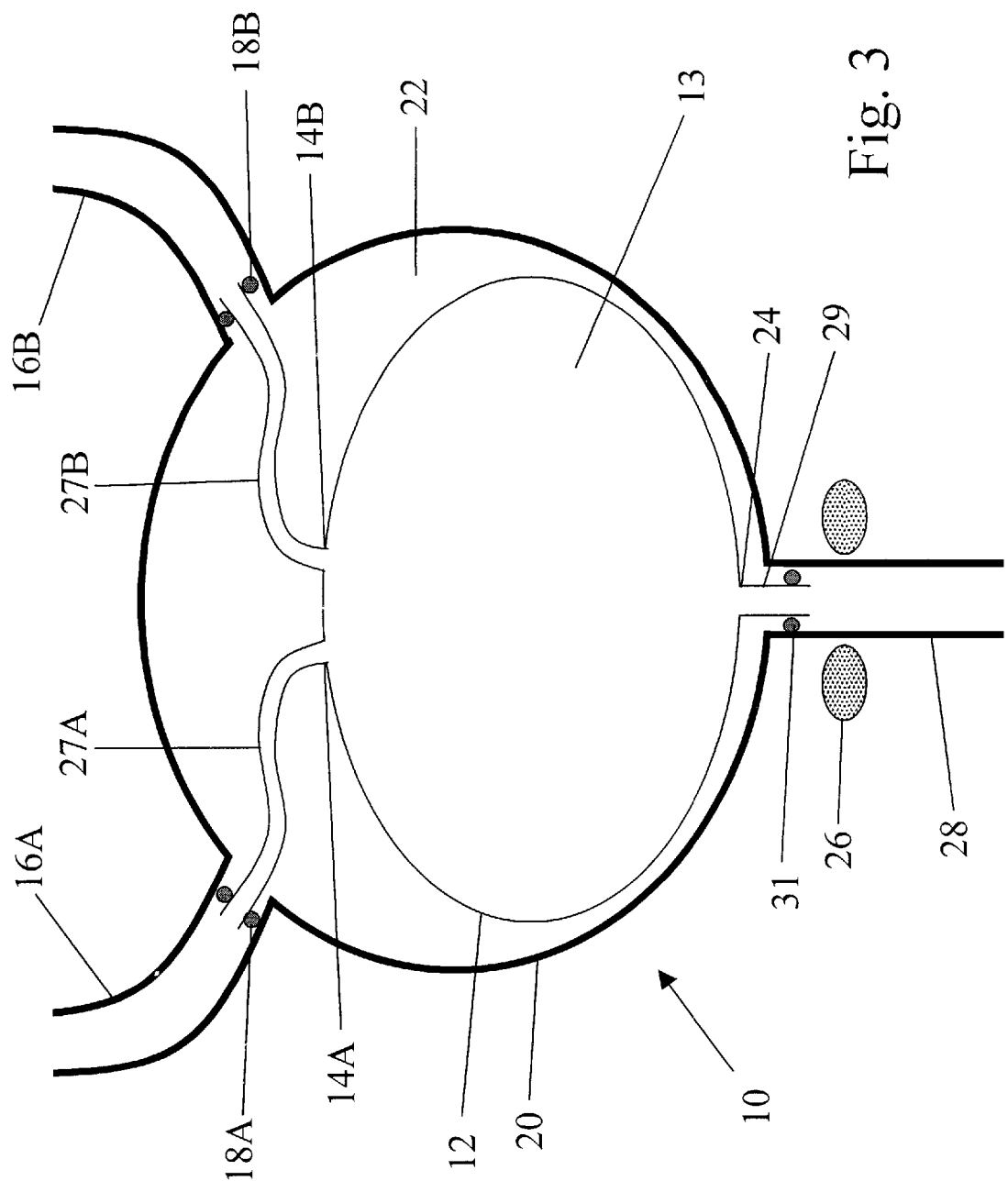
FIG. 3 is a depiction of a bladder liner that is designed to fit inside a patient's urinary bladder. Three catheters lead from the bladder liner. The two catheters that are situated on one side of the bladder liner are sealed to the patient's two ureters. The third catheter, which is generally situated on the opposite side of the bladder liner, is sealed to the patient's urethra so as not to extend past the urinary sphincter. This device provides for patient continence by maintaining sphincter function.

In an alternative embodiment shown in FIG. 3, the outlet catheter 29 of the urinary bladder liner 12 is adapted to sealably connect to the wall of the urethra 28 prior to the point in the urethra 28 that is constricted by the urinary sphincter 26. The catheter 29 may be sealably connected by the use of bioadhesive(s) or o-ring(s) 31. Other possible seals include radial fins, balloons, and collagen cuffs.

Figure 4:
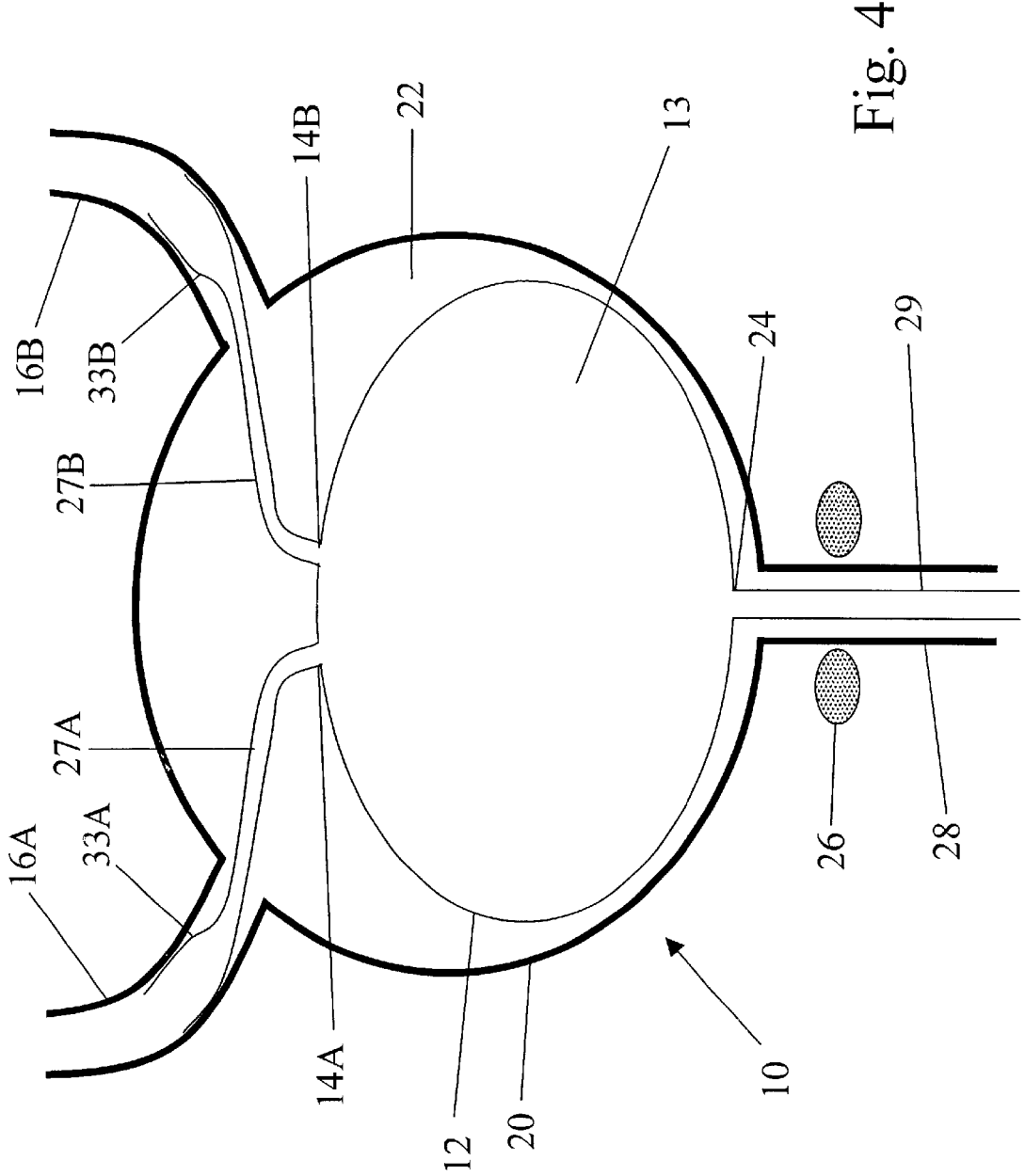
FIG. 4 is a depiction of a bladder liner that is designed to fit inside a patient's urinary bladder. Three catheters lead from the bladder liner. The two catheters that are situated on one side of the bladder liner are inserted into the patient's two ureters. The two catheters inserted in the ureters expand to the diameter of the ureter forming a strong and fluid-impervious junction. The third catheter, which is generally situated on the opposite side of the bladder liner, extends into the patient's urethra past the urinary sphincter. This device provides for patient continence by maintaining sphincter function.

In various embodiments of the invention, the sealable connections 18A,B, 31 may be produced by the use of at least one nonpermanent biocompatible adhesive or sealant. The adhesive forms a fluid-impermeable seal that prevents urine from entering into the urinary bladder 22. Suitable bioadhesives include fibrin glue, cynoacrylates, and collagen cuffs. In an alternative embodiment shown in FIG. 4, the sealable connections 33A,B between catheters 27A,B and a luminal space in the body can be produced by the expansion of the catheters' outer diameter. The expanded diameters 33A,B of the catheters 27A,B press against the walls of a luminal space in the body such as the ureters 16A,B or urethra 28. The catheters 27A,B are held in place in the ureters 16A,B or urethra 28 by the mechanical force exerted by the expanded ends 33A,B of the catheters. Such a connection also provides a liquid-impermeable seal.

Figure 5A:
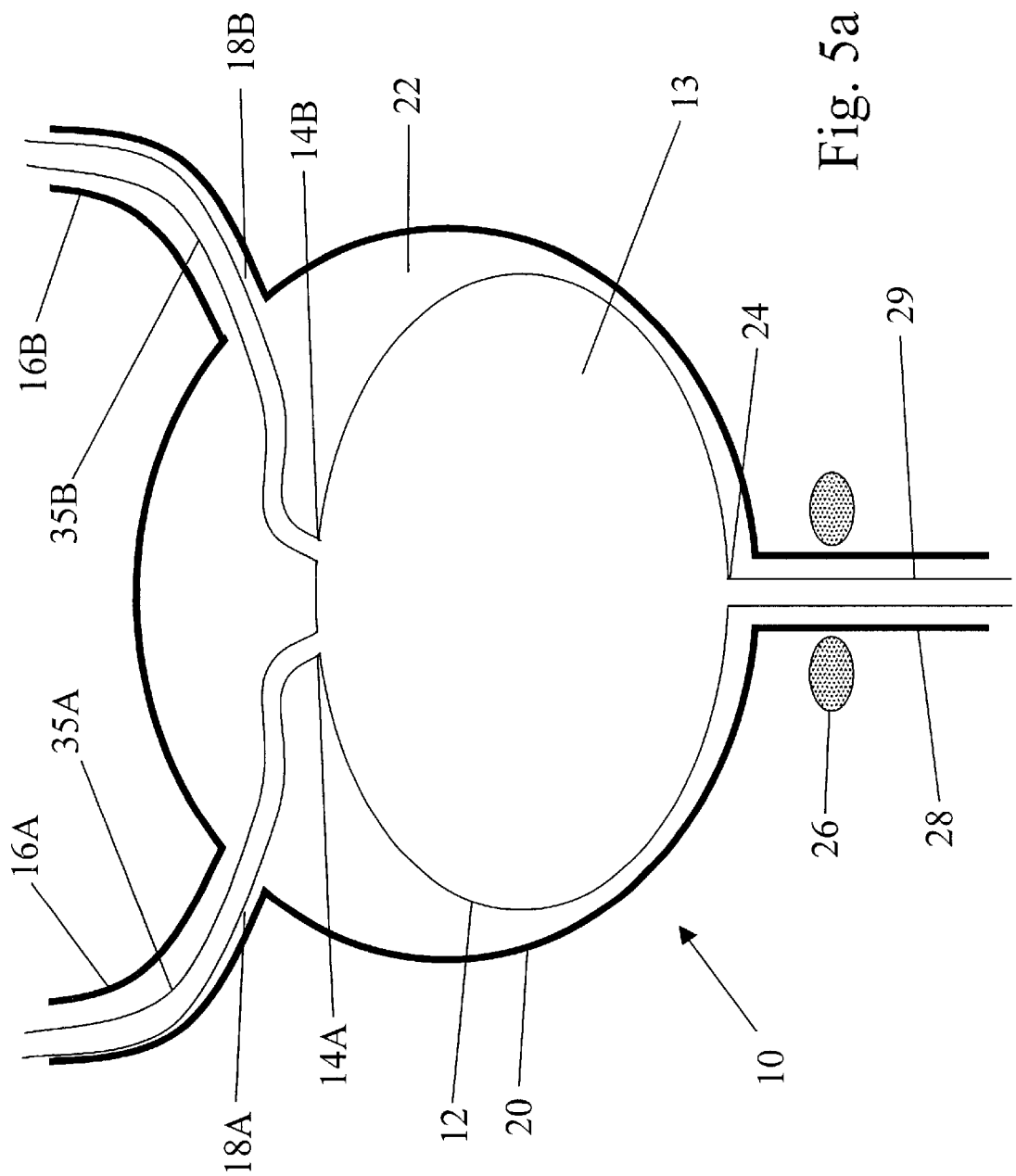
FIG. 5a is a depiction of a bladder liner that is designed to fit inside a patient's urinary bladder. Three catheters lead from the bladder liner. The two catheters that are situated on one side of the bladder liner extend into the patient's two ureters and continue up and into the kidneys, where the catheters coil into a pigtail formation that prevents migration of the catheters out of the kidney. The third catheter, which is generally situated on the opposite side of the bladder liner, extends into the patient's urethra past the urinary sphincter. This device provides for patient continence by maintaining sphincter function.
Figure 5B:
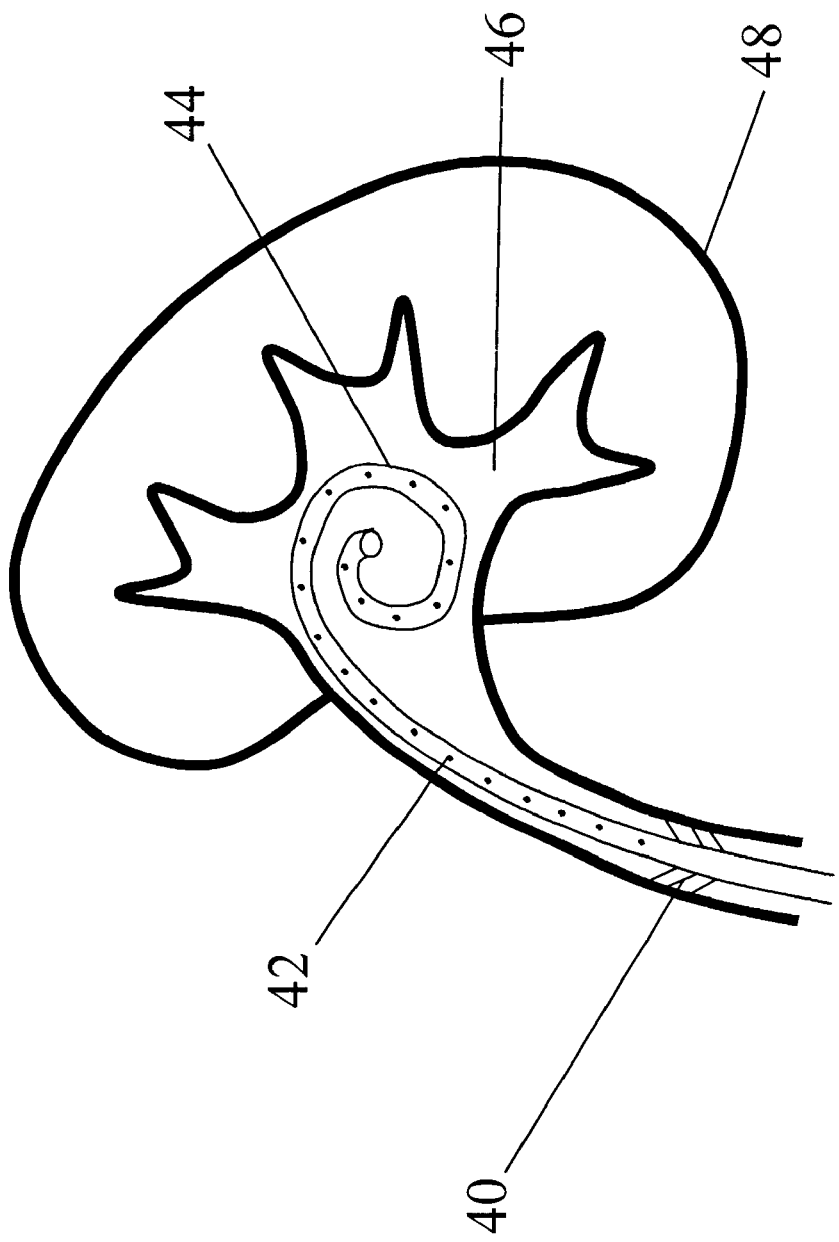
FIG. 5b is a depiction of a coiled end of the catheters of FIG. 5a that reside in the kidney. The pigtail portion of the catheter prevents the migration of the catheters down the ureter and into the urinary bladder. Fins or seals on the exterior surfaces of the catheters prevent flow of urine down the ureter and force the urine flow into the catheters.

In the embodiment shown in FIGS. 5a and 5b, a bladder liner 12 made from an impermeable, but highly flexible and elastic material is designed to fit inside the urinary bladder 22. The liner 12 includes a reservoir 13 formed therein and is constructed with two catheters 35A,B that are connected to the two inlet orifices 14A,B of the bladder liner 12. The catheters 35A,B extend up the respective ureters 16A,B and into the kidneys 48. FIG. 5b depicts the ends of the catheters 35A,B that are preformed as circular coils 44, the purpose of which is to prevent the catheters 35A,B from migrating down the ureters 16A,B towards the urinary bladder 22. The ends of the input catheters 35A,B posses a plurality of drainage holes 42, so urine can easily enter the catheters 35A,B. Below (towards the urinary bladder) the drainage holes 42, the catheters 35A,B possess a plurality of fins 40 mounted on the exterior surfaces of the catheters 35A,B. The fins 40 are designed to form a liquid-impermeable seal with a ureter wall. The liner 12 is also constructed with an outlet catheter 29 connected to an outlet orifice 24. The outlet catheter 29 is adapted to extend through the urethra 28 to direct the flow of urine through the urethra 28 and out of the body.

In various embodiments of the invention, the urinary bladder liner 12 is constructed of a non-elastic material or a highly flexible and pliant material. A non-elastic bladder liner 12 will not expand to the dimensions of the urinary bladder 22, and thus will not apply pressure to the urinary bladder wall 20 when the bladder liner 12 is at or near capacity. Alternatively, the liner 12 can be constructed of a highly flexible, pliant and elastic material, which allows the liner 12 to expand to the dimensions of the urinary bladder 22. An exterior surface of the urinary bladder liner 12 may be coated with heparin or a heparin-like drug to promote the healing of the bladder wall 20 at points where the bladder wall 20 and the bladder liner 12 make contact. In addition, the exterior surface of the urinary bladder liner 12 may be coated with a slippery material such as, but not limited to, a hydrogel to reduce chafing or irritation of the bladder wall 20 at points where the bladder wall 20 and the bladder liner 12 make contact.

Figure 6:
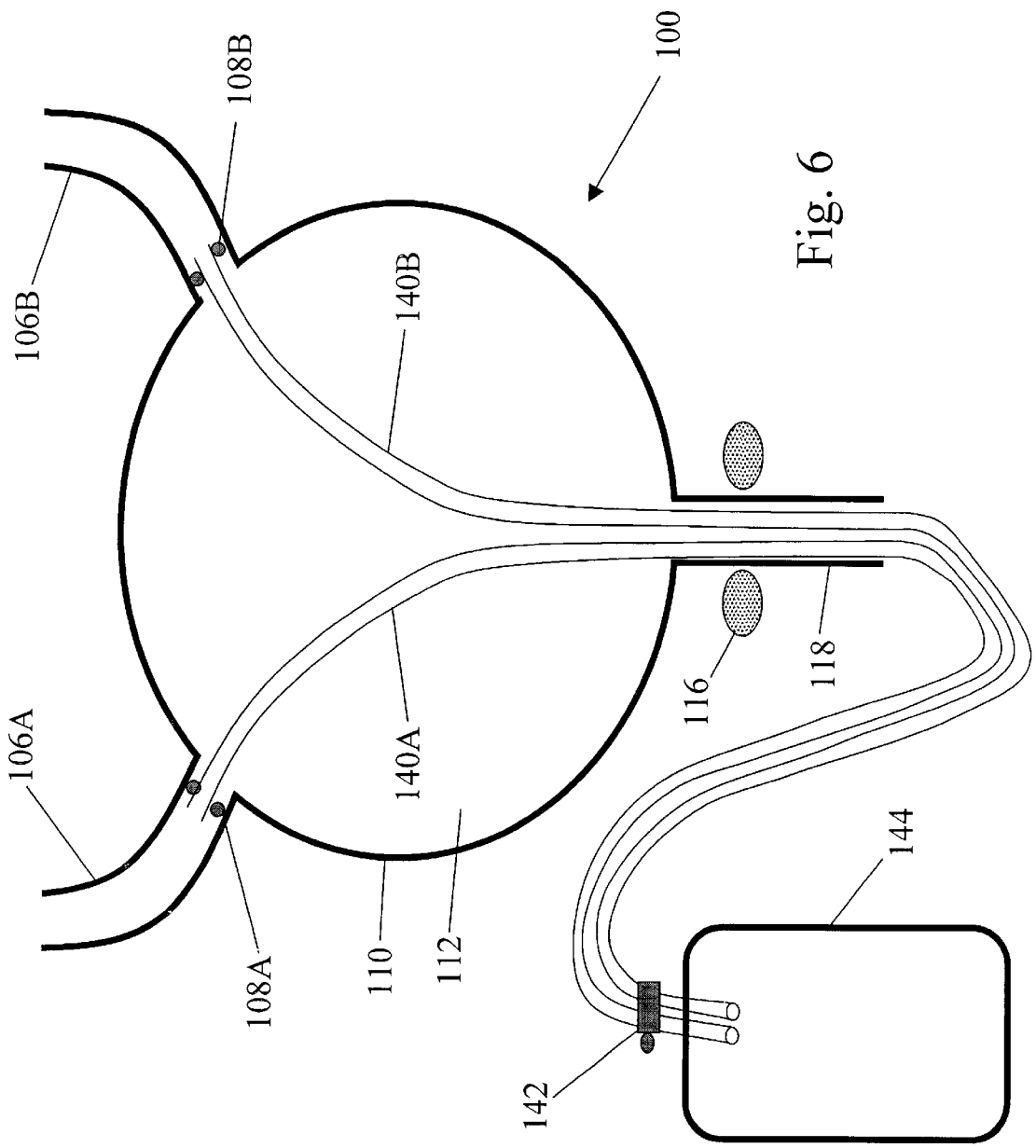
FIG. 6 is a depiction of a catheter device that is designed to fit inside a patient's urinary bladder. Two catheters are sealed to the patient's two ureters and extend through the urinary bladder and the urethra to the outside of the patient's body where both catheters empty into an external urine container. A shutoff valve prevents the flow of urine from one or both catheters. Normal sphincter function is lost with this device.

Another embodiment of a device 100 in accordance with the invention is shown in FIG. 6. Two catheters 140A,B are inserted into the two openings of the ureters 106A,B in the urinary bladder 112 and are adapted to sealably connect to the ureter walls. The two catheters 140A,B extend through the urinary bladder 112 and through the urethra 118 exiting the body. The catheters 140A,B lead into an external collection container 144. A valve 142 on each catheter 140A,B functions to block the flow of urine while removing or replacing the urine collection container 144. Alternatively, a single valve 142 may be used to isolate the flow of urine from the catheters 140A,B to the collection container 144. The seals 108A,B used to seal the catheters 140A,B to the ureter 106A,B may be biocompatible adhesive(s), o-ring(s), fins or catheters that expand to press against the wall of the ureters 106A,B.

Figure 7:
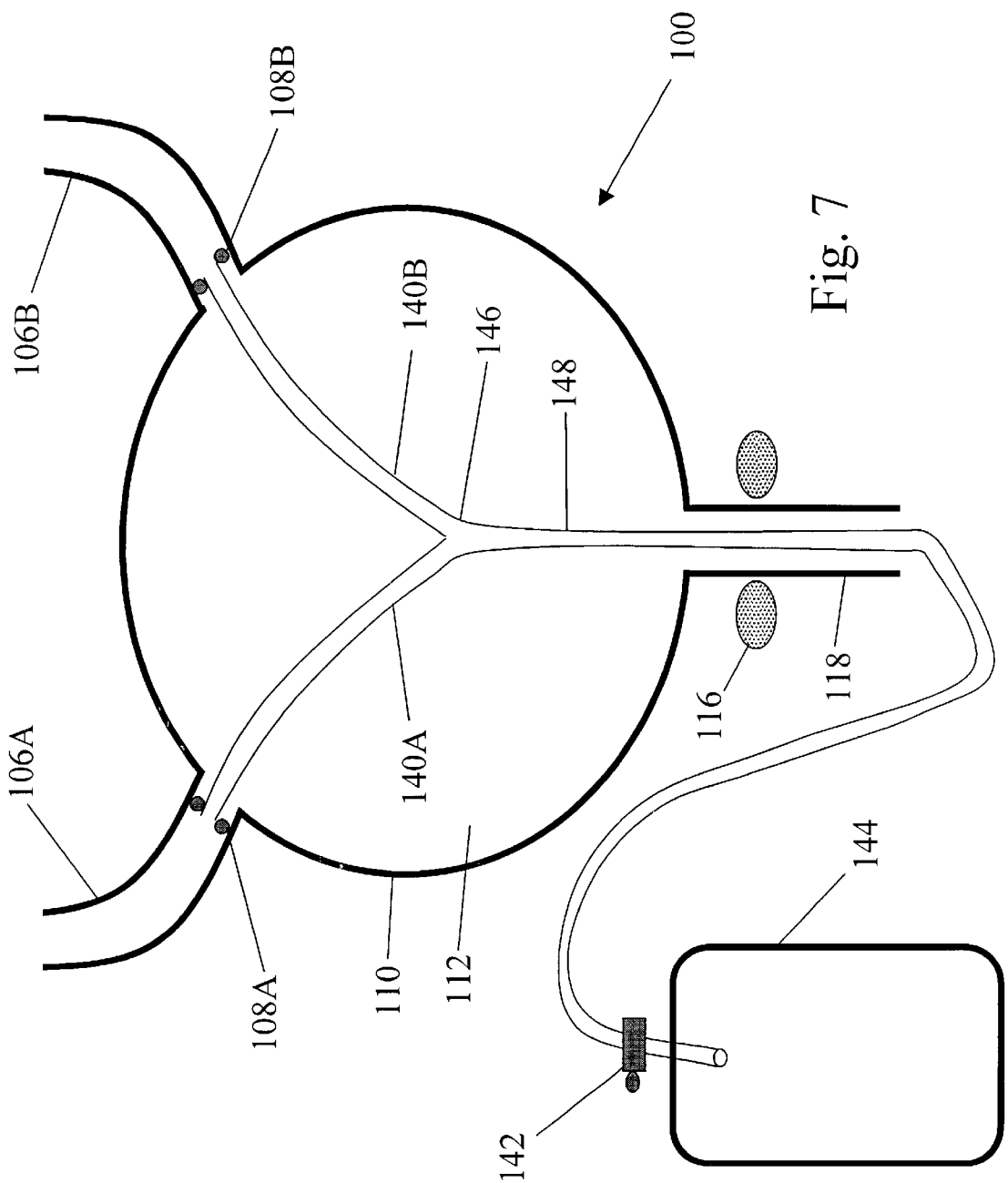
FIG. 7 is a depiction of a catheter device that is designed to fit inside a patient's urinary bladder. Two catheters are sealed to the patient's two ureters and extend into the urinary bladder where they join to form one catheter. The resulting single catheter extends through the patient's urethra to the outside of the patient's body where it empties into an external urine container. A shutoff valve prevents the flow of urine from the catheter. Normal sphincter function may be lost with this device.

A further embodiment of the device 100 is shown in FIG. 7. Two catheters 140A,B join to form a third catheter 148 in the urinary bladder 112. The third catheter 148 extends through the urethra 118 and into an external collection container 144. In this embodiment, only the third catheter 148 is present in the urethra 118 during the normal functioning of the apparatus, thus providing greater comfort to the patient. The third catheter 148 includes a valve 142 disposed between the distal end of the urethra 118 and the distal end of the catheter 148 that functions to block the flow of urine while removing or replacing the urine collection container 144. The seals 108A,B used to seal the catheters 140A,B to the ureters 106A,B may be biocompatible adhesive(s), o-ring(s), or catheters that expand to press against the wall of the ureters 106A,B. The catheters 140A,B and 148 may be joined at a catheter junction 146 by use of a fitting or bonding, or may be formed as a single assembly. The catheters 140A,B 148 and catheter junction 146 are composed of materials comprising biocompatible plastics, such as vinyl, polyethylene, PVC, silicone, ethylene vinyl acetate, and polypropylene.

Figure 8:
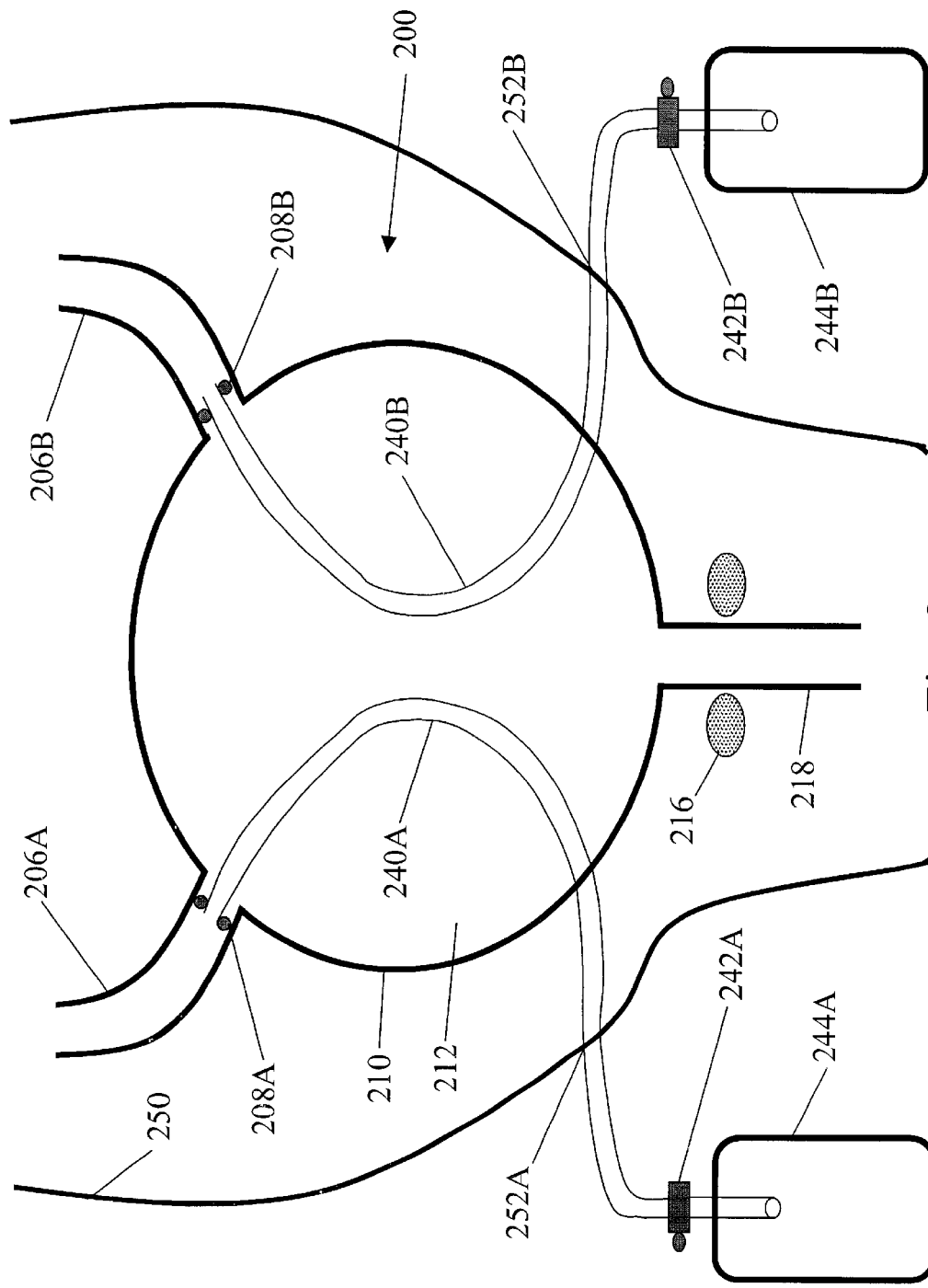
FIG. 8 is a depiction of a catheter device that is designed to fit inside a patient's urinary bladder. Two catheters are sealed to the patient's two ureters and each extends through a suprapubic incision in the patient's abdominal wall to the outside of the patient's body where both catheters empty into external urine containers. A shutoff valves prevent the flow of urine from each catheter. Normal sphincter function is maintained with this device.

Yet another embodiment of a device 200 in accordance with the invention is shown in FIG. 8. Two catheters 240A,B are inserted into the two openings of the ureters 206A,B in the urinary bladder 212 and are adapted to sealably connect to the ureter walls. The two catheters 240A,B extend through the urinary bladder 112 and out of the patient's body through the bladder and abdominal walls. Specifically, the catheters 240A,B pass through one or more suprapubic incisions 252A,B in the patient's abdomen 250. Generally, suprapubic incisions are incisions situated or performed superior to the patient's pubic arch. This embodiment eliminates urine drainage through the urethra 218, thereby eliminating irritation of the urethra 218 and urinary sphincter 216 from the presence of the catheters 240A,B. With no catheters 240A,B present in the urethra 218, the urinary sphincter 216 functions normally, thus providing greater comfort to the patient. Each catheter 240A,B leads into an external collection container 244A,B. A valve 242A,B on each catheter 240A,B functions to block the flow of urine while removing or replacing the urine collection container 244A,B.

Alternatively, the catheters 240A,B may pass through a single suprapubic incision 252 and connect to a single external collection container 244. In which case, a single valve 242 may be used to isolate the flow of urine from the catheters 240A,B to the collection container 244. In addition, the seals 208A,B used to seal the catheters 240A,B to the ureter 206A,B may be biocompatible adhesive(s), o-ring(s), fins or catheters that expand to press against the wall of the ureters 206A,B.

Figure 9:
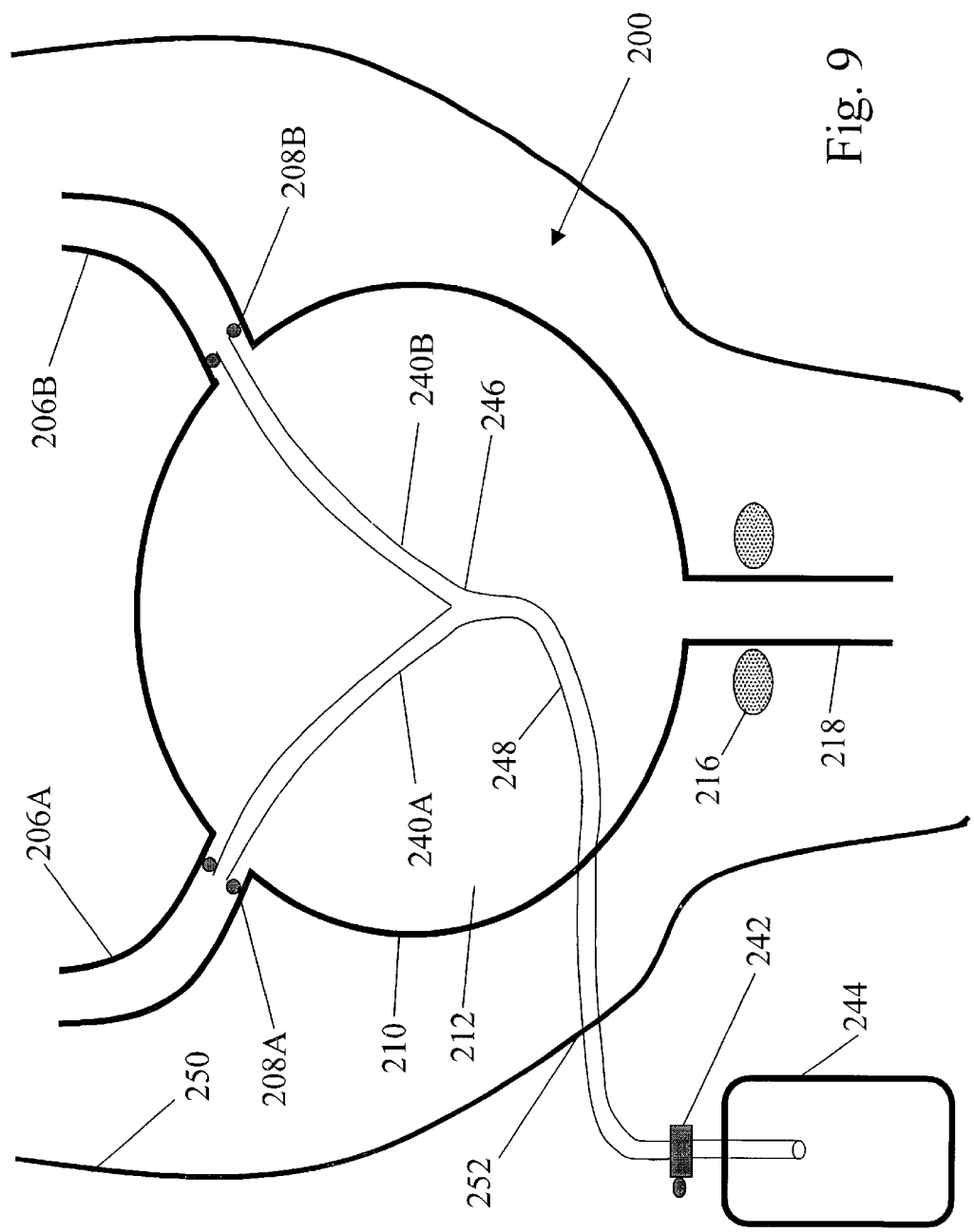
FIG. 9 is a depiction of a catheter device that is designed to fit inside a patient's urinary bladder. Two catheters are sealed to the patient's two ureters and extend into the urinary bladder where they join to form one catheter. The resulting single catheter extends through a suprapubic incision in the patient's abdominal wall to the outside of the patient's body where it empties into an external urine container. A shutoff valve prevents the flow of urine from the catheter. Normal sphincter function is maintained with this device.

A further embodiment of the device 200 is shown in FIG. 9. Two catheters 240A,B join to form a third catheter 248 in the urinary bladder 212. The third catheter 248 extends through the patient's bladder and abdominal walls and into an external collection container 244. Specifically, the third catheter 248 extends through a suprapubic incision 252 in the patient's abdomen 250. This embodiment also eliminates irritation of the urethra 218 and urinary sphincter 216, allows the urinary sphincter 216 to function normally, and provides greater comfort to the patient. The third catheter 248 includes a valve 242 disposed between the suprapubic incision 252 and the distal end of the catheter 248 that functions to block the flow of urine while removing or replacing the urine collection container 244. Further, the seals 208A,B used to seal the catheters 240A,B to the ureters 206A,B may be biocompatible adhesive(s), o-ring(s), or catheters that expand to press against the wall of the ureters 206A,B. The catheters 240A,B and 248 may be joined at a catheter junction 246 by use of a fitting or bonding, or may be formed as a single assembly. The catheters 240A,B 248 and catheter junction 246 are composed of materials comprising biocompatible plastics, such as vinyl, polyethylene, PVC, silicone, ethylene vinyl acetate, and polypropylene.

Methods according to the invention include treating urinary bladder diseases by isolating urine from the urinary bladder wall by the use of the aforementioned devices and treating the patient with appropriate medications. Appropriate medications include oral medications comprising sodium pentosanpolysulfate, amitripyline, imipramine, hydroxyzine dihydrochloride, hydroxyzine hydrochloride, hyoscyamine sulfate, hyosyamine, oxybutynin chloride, flavoxate, urised, or phenazopyridine hydrochloride. In an alternative method, appropriate medications include topically applied medications comprising DMSO, heparin, sodium oxychlorosene, lidocaine, hydrocortisone sodium succinate, sodium bicarbonate, capsaicin, hyaluronic acid, silver nitrate, or bacillus of Calmette and Guerin (BCG). These medications are instilled between the bladder liner and bladder wall to achieve topical therapy to the inner wall of the bladder.

Having described certain embodiments of the invention, it will be apparent to those of ordinary skill in the art that other embodiments incorporating the concepts disclosed herein may be used without departing from the spirit and scope of the invention. The described embodiments are to be considered in all respects as only illustrative and not restrictive.

What is claimed is:

1. A medical device adapted to fit within a patient's urinary bladder, the device comprising:
   a liner comprising:
      a reservoir;
      a first inlet and a second inlet in fluidic communication with the reservoir, each inlet sealably connectable to a respective end of one of the patient's two ureters to pass urine into the reservoir; and
      an outlet in fluidic communication with the reservoir and extending into the patient's urethra to permit voiding of urine from the reservoir, wherein the liner fits within the urinary bladder and substantially isolates urine from the urinary bladder.

2. The liner of claim 1, wherein the first and second inlets connect to inlet catheters that are adapted to sealably connect to the respective ends of the ureters.

3. The liner of claim 1, wherein the outlet is adapted to sealably connect to the urethra.

4. The liner of claim 1, wherein the outlet is adapted to extend through a urinary sphincter.

5. The liner of claim 1, wherein the outlet connects to an outlet catheter that is adapted to extend through a urinary sphincter.

6. The liner of claim 5, wherein the outlet catheter comprises a material sufficiently flexible to facilitate compression by the urinary sphincter.

7. The liner of claim 1, wherein the sealable connections comprise at least one biocompatible adhesive.

8. The liner of claim 2, wherein the sealable connections comprise an expandable wall at an end of each inlet catheter that contacts the ureters so as to fix the catheter ends in place and form a liquid-impermeable seal.

9. The liner of claim 2, wherein the inlet catheters are adapted to extend through the ureters and into the patient's kidneys.

10. The liner of claim 1, wherein the liner is made of a pliant material.

11. The liner of claim 1, wherein the liner is made of a material selected from the group consisting of vinyl, polyethylene, PVC, EVA, silicone, latex, and polypropylene.

12. The liner of claim 1, wherein an outer surface of the liner is coated with at least one of heparin and a heparin-like drug.

13. The liner of claim 1, wherein the liner comprises a material that stretches and shrinks.

14. The liner of claim 1, wherein an outer surface of the liner is coated with a hydrogel.

15. The liner of claim 2, wherein the outlet connects to an outlet catheter that is adapted to extend through the urethra.

16. The liner of claim 9, wherein distal ends of the inlet catheters are coiled to fit in a kidney basin.

17. The liner of claim 16, wherein the inlet catheters include a plurality of fins mounted on exterior surfaces of the catheters and adapted to form a liquid-impermeable seal with a wall of each ureter.

18. An apparatus for isolating urine from a patient's urinary bladder, the apparatus comprising:
   a first catheter positionable in the patient's first ureter, the first catheter including a proximal end and a distal end, the proximal end of the first catheter including a ureter to catheter seal, the distal end of the first catheter being capable of passing through the patient's urinary sphincter; and
   a second catheter positionable in the patient's second ureter, the second catheter including a proximal end and a distal end, the proximal end of the second catheter including a ureter to catheter seal, the distal end of the second catheter being capable of passing through the patient's urinary sphincter and the distal ends of the first and second catheters being capable of connection to an external urine collection container.

* * * * *

UNITED STATES PATENT AND TRADEMARK OFFICE
CERTIFICATE OF CORRECTION

PATENT NO.    : 6,648,863 B2
DATED         : November 18, 2003
INVENTOR(S)   : Reever It is certified that error appears in the above-identified patent and that said Letters Patent is hereby corrected as shown below:

<u>Title page,</u>
Item [56], References Cited, OTHER PUBLICATIONS, add the following reference:

-- Parsons, "Interstitial Cystitis: New Concepts in Pathogenesis, Diagnosis, and Management" <u>San Diego '98 American Urological Association</u>, June 4, 1998, pp. 1-23 --

<u>Column 10,</u>
Line 21, replace claim 18 with the following:

18. The liner of claim 1, wherein the sealable connections comprise o-rings.

Signed and Sealed this

Sixth Day of April, 2004

JON W. DUDAS
*Acting Director of the United States Patent and Trademark Office*